United States Patent [19]

Newton et al.

[11] 4,094,320
[45] June 13, 1978

[54] ELECTROSURGICAL SAFETY CIRCUIT AND METHOD OF USING SAME

[75] Inventors: David W. Newton; Frank A. Alford, both of Boulder, Colo.

[73] Assignee: Valleylab, Inc., Boulder, Colo.

[21] Appl. No.: 721,821

[22] Filed: Sep. 9, 1976

[51] Int. Cl.² .................. A61B 17/36; A61N 3/00
[52] U.S. Cl. ............................................. 128/303.14
[58] Field of Search ................. 128/303.13, 303.14, 128/303.17, 303.18, 2.1 P

[56] References Cited

U.S. PATENT DOCUMENTS

| 3,675,655 | 7/1972 | Sittner | 128/303.14 |
| 3,683,923 | 8/1972 | Anderson | 128/303.14 |
| 3,885,569 | 5/1975 | Judson | 128/303.14 |
| 3,897,787 | 8/1975 | Ikuno et al. | 128/303.14 |
| 3,946,738 | 3/1976 | Newton et al. | 128/303.14 |

FOREIGN PATENT DOCUMENTS

| 2,602,517 | 7/1976 | Germany | 128/303.13 |
| 1,439,302 | 1/1969 | Germany | 128/303.14 |
| 2,439,587 | 2/1975 | Germany | 128/2.1 P |

Primary Examiner—Kyle L. Howell
Assistant Examiner—Lee S. Cohen
Attorney, Agent, or Firm—Gerald J. Ferguson, Jr.; Joseph J. Baker

[57] ABSTRACT

An improved electrosurgical safety circuit where the currents in the active and patient leads are monitored, the monitored currents being respectively rectified and then subtracted from one another. Whenever the active current exceeds the patient or return current by an amount corresponding to a dynamically variable threshold, an appropriate measure is taken such as the sounding of an alarm and/or the de-energization of the electrosurgical generator. The dynamic threshold varies in accordance with the level of the signal applied to the patient and compensates for leakage current through stray capacitance from the active lead to ground.

The patient lead is substantially grounded at radio frequencies through a frequency sensitive network. The frequency sensitive network may include a capacitor, the value of which is such as to provide the foregoing frequency response. Since as small a capacitor as possible must be used to provide a high impedance at low frequencies, and since the radio frequency voltage across the capacitor must be kept low to thereby keep the voltage patient low at radio frequencies, a further network is employed to enable the use of a small capacitor while at the same time decreasing the effective voltage thereacross whereby protection of the patient is enhanced.

15 Claims, 1 Drawing Figure

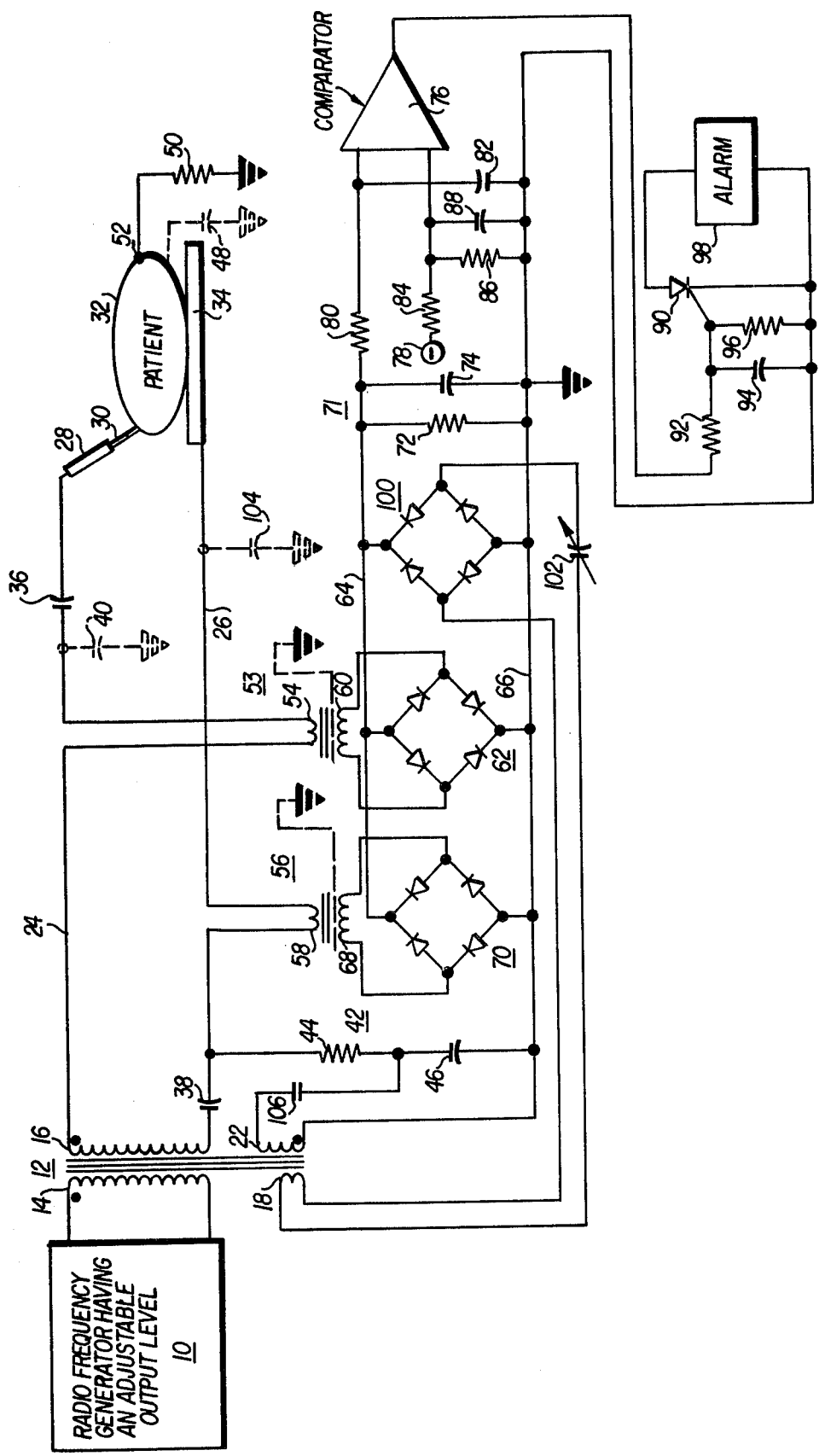

ELECTROSURGICAL SAFETY CIRCUIT AND METHOD OF USING SAME

REFERENCE TO RELATED APPLICATION

The present application is related to a U.S. application entitled "Safety Monitoring Circuit For Electrosurgical Unit" assinged Ser. No. 520,269, filed Nov. 4, 1974 by David W. Newton, one of the co-inventors of the present application and assigned to the same Assignee, the foregoing application being hereby incorporated herein by reference.

BACKGROUND OF THE INVENTION

1. Field of the Invention

This invention is directed to safety circuits for use with electrosurgical apparatus and to a method of using such circuitry.

2. Discussion of the Prior Art

Various safety circuits have been described in the prior art for use with electrosurgical systems. For example, in U.S. Pat. No. 3,683,923, granted to Robert K. Anderson, circuitry for detecting, inter alia, a discontinuity in the patient circuit is described where the patient circuit includes the patient or indifferent electrode and the patient lead connected thereto. Such a discontinuity can occur, for example, whenever the patient loses contact with the patient electrode or a break occurs in the patient lead. The current from the active electrode will seek ground through an alternate current return path whenever a patient circuit discontinuity occurs. Such a path may be provided through a monitoring electrode attached to the patient's body or any other grounded object in inadvertent contact therewith. Since a monitoring electrode or the like may contact the patient over a very small area, the current density thereat will be quite high thereby tending to burn the patient. Further, since the monitoring electrode or the like may be covered by a sheet, the burning may occur for a substantial period of time before it is detected. Hence, it is very important that appropriate means be provided to detect a discontinuity in the patient circuit and take appropriate action upon the detection thereof such as the sounding of an alarm and/or the de-energization of the generator.

The aforesaid U.S. Pat. No. 3,683,923, which is incorporated herein by reference, detects a discontinuity in the patient circuit by taking the difference between the radio frequency current in the active lead and that in the patient lead. Whenever this difference exceeds a predetermined threshold, an alarm is sounded. In particular, the alarm is sounded whenever the active lead current exceeds the patient lead current by the threshold value or vice versa — that is, whenever the patient lead current exceeds the active lead current. The foregoing results from the fact that the difference is taken between the radio frequency currents in the active and patient leads. However, the dangerous condition corresponding to a patient circuit discontinuity occurs when the active lead current exceeds the patient lead current. In fact, the radio frequency patient lead current can exceed the radio frequency active lead current without danger to the patient. Thus, if two electrosurgical generators with two respective instruments are in contact with a patient's body as is sometimes the case and one of the instruments is active and the other is idle, the current from the active instrument will divide between the patient leads for the two generators whereby the patient current for the idle generator will exceed that in the active lead thereof. With a safety circuit as disclosed in the aforementioned Anderson patent or the aforementioned Newton patent application, the aforesaid condition would generate a nuisance alarm — that is, an alarm when the patient is not in danger.

It is thus a primary purpose of this invention to provide an improved safety circuit for use with an electrosurgical generator which is sensitive only to an excess of active lead current over patient lead current to thereby detect a discontinuity in the patient lead circuit without generating nuisance alarms whenever the patient lead current exceeds that of the active lead.

In the aforementioned application Ser. No. 520,269, a current sensing device is employed in the grounding connection of the patient lead where, if a predetermined current is sensed, an alarm condition is signalled. However, whenever coagulation waveforms of high crest factor (defined as the peak vaue in voltage or current divided by the rms value) are employed, the magnitude and higher harmonic components of the generator output signal will increase thereby increasing the active lead leakage current through the stray capacitance from the active lead to ground. This current will also be sensed by the current sensor and tend to generate a nuisance alarm since the current is not dangerous to the patient.

It is thus a further object of this invention to provide a safety circuit of the foregoing type wherein a dynamically variable threshold is employed to thereby permit the lowest possible threshold for sounding an alarm without the production of nuisance alarms associated with the use of high performance waveforms such as coagulation waveforms having high peak to peak voltages and crest factors.

As brought out in the aforesaid patent application Ser. No. 520,269, it is desirable to substantially ground the patient lead for radio frequency currents to thereby prevent the elevation of the patient to an undesirable potential. Thus, anesthesiologists quite often like to touch the patient during a surgical procedure to monitor temperature, pulse rate and the like. Since the area of contact with the patient, due to a light touch, is quite small, the person touching the patient will experience a slight burning sensation if the patient is elevated to an undue potential. This burning sensation although typically not dangerous is often disconcerting. If the patient lead is isolated from ground at radio frequencies, the abovementioned leakage currents from the active lead to ground can raise the potential of the patient lead with respect to ground due to the coupling of this current through stray capacitance from the patient lead to ground. The active lead to ground leakage current, as stated above, increases with increasing crest factor, for example. Hence, whenever a high performance level is desired, it is difficult to use an isolated output circuit since the patient lead potential rises to an undesirable level and hence the patient lead msut be substantially grounded at radio frequencies. Further, if the active electrode of an isolated output circuit accidentally contacts a grounded object, the patient would be raised to the full output potential of the generator if the patient were not kept at about ground potential for radio frequency current. Thus, this is a further reason for grounding the patient lead at radio frequencies.

However, grounding of the patient lead is undesirable at low frequencies such as the 60 Hz power frequency. That is, if the patient comes in contact with, for example, a faulty piece of equipment which is at power frequency potential, this potential could be conducted through the patient to the grounded patient lead thereby subjecting the patient to the extreme danger of electrocution. Hence, at power frequencies and the like it is desirable to effectively isolate the patient lead from the ground and thus not establish a path where high, power frequency voltages can pass through a patient upon inadvertent contact with a faulty piece of equipment. In the aforementioned Newton patent application, the foregoing is effected by providing a frequency sensitive network between the patient lead and ground whereby a low impedance is presented to radio frequency currents and a high impedance is presented to power frequency currents and the like. This can be achieved by the appropriate selection of a capacitor, the value of which is low enough to present a high impedance at the low frequencies and high enough to present a low impedance at the radio frequencies where radio frequencies for the purposes of this application extend approximately from 200 kilohertz to 5 megahertz although there is no intent to be limited to this particular range. A limitation on how small a capacitor may be employed is that of the voltage on the patient lead. As stated above, this voltage must not raise the potential of the patient too high. As also stated above, when using electrosurgical generators operating at a high level of performance, high voltage levels are typically employed. Thus, there is a tendency for the voltage across the capacitor to increase with these higher voltages levels.

Hence, it is a further object of this invention to provide circuitry for decreasing the effective voltage across the capacitor in a frequency sensitive network of the type described above whereby a smaller capacitor may be used while, at the same time, decreasing the voltage thereacross.

These and other objects of the invention will become apparent from a reading of the following specification and claims taken together with the drawing.

BRIEF DESCRIPTION OF THE DRAWING

The drawing is a schematic diagram of an illustrative embodiment of the invention.

DETAILED DESCRIPTION OF THE PREFERRED EMBODIMENT

Referring to the drawing, a radio frequency generator 10 drives an isolation transformer 12 comprising a primary winding 14 and three secondary windings 16, 18 and 22. The output circuit connected to secondary winding 16 includes an active lead 24 and a patient or return lead 26. The active lead is connected to an electrosurgical instrument 28 having an active electrode 30 suitable for effecting surgical procedures on a patient 32. The patient is normally disposed on an indifferent or patient electrode 34 and the current from electrode 30 normally passes through the patient to the large area, patient electrode 34 and then back to winding 16 via lead 26. Capacitors 36 and 38 are respectively disposed in leads 24 and 26 and present a high impedance to the circulation of "faradic" current in the patient. These currents are subharmonics resulting from the rectification process occurring at the active electrode patient interface, the subharmonics being of a low frequency and potentially hazardous to the patient. However, due to the impedance presented to these currents by the capacitors 36 and 38, their magnitude is kept at a nonhazardous level.

If a discontinuity occurs in the patient circuit including the patient lead 26 and terminal 34, a potentially dangerous situation for the patient can arise. Typically, such a discontinuity may arise if the patient loses contact with electrode 34 or there is a break in lead 26 or in the connection of this lead to terminal 34 or winding 16. Due to stray capacitance 40 from the active lead to ground, the current from active electrode 30 will also seek ground. As will be brought out in more detail hereinafter, lead 26 is maintained near ground potential by a frequency sensitive alternate current return path or network generally indicated at 42 comprising resistor 44 and capacitor 46. Thus, as long as the patient circuit is in tact, the current through the patient will mainly flow to lead 26 through electrode 34. However, if a discontinuity occurs, this current path is disrupted and the current in the patient will seek another path to ground. This may be through the capacitance 48 which represents the capacitance between the patient's body and ground. However, if the patient is in inadvertent contact with a grounded object, this lower impedance path will be preferred and is indicated at 50. If the point of contact 52 between the patient and the grounded object is small, the current density at this point will be high with the attendant probability that a burn will occur at this point particularly if the discontinuity in the patient circuit and the inadvertent contact with the grounded object 50 goes undetected for a long time. This could quite likely happen if the contact point were covered by a sheet or the like.

In order to avoid the foregoing problem, circuitry is provided to sound an alarm or take some other appropriate measure upon detection of a discontinuity in the patient circuit. It should first be noted that the current from the active electrode will normally divide between two paths, the first extending through the patient and patient electrode 34 to lead 26 and thus, back to winding 16 and the second extending through capacitor 48 to ground and then from ground through capacitor 46 and resistor 44 again to lead 26. The current in this second path is normally quite small and thus the current flowing from electrode 34 is substantially equal to the current flowing from electrode 30. However, when a discontinuity occurs in the patient lead, the current flowing from electrode 34 will be substantially less than that flowing from electrode 30 and it is this principle that is utilized to detect a discontinuity in the patient circuit. The same principle is utilized in the aforementioned Anderson U.S. Pat. No. 3,683,923.

Thus, a current transformer 53 having a grounded shield monitors the current in active lead 24 where the primary winding 54 is in series connection with the lead. A similar current transformer 56 monitors the current in the patient lead 26 and its primary winding 58 is in series connection with this lead. The radio frequency current flowing in the active lead induces a current through the secondary coil 60 of transformer 53 which is rectified by a diode bridge 62 disposed between lead 64 and grounded lead 66. In a similar manner, the current flowing in the patient lead 26 induces a current in the secondary winding 68 of transformer 56, this current being rectified by a diode bridge 70, also disposed between leads 64 and 66. The bridges 62 and 70 are polarized in different directions so that their respective contributions to the currents flowing in leads 64 and 66 normally substantially cancel each other out since these contributions are substantially equal and in opposite directions.

To smooth the current flowing through lead 64 a filter 71 comprising resistor 72 and capacitor 74 is employed and the potential across resistor 72 is used to trigger a comparator 76 whenever the potential across the resistor exceeds that established by a reference potential 78. A resistor 80 and capacitor 82 couples the potential across resistor 72 to comparator 76 while resistors 84 and 86 and capacitor 88 couple the reference potential to the comparator.

The output of the comparator triggers an SCR 90 through a coupling network comprising resistor 92, capacitor 94 and resistor 96. The triggering of the SCR causes appropriate action to be taken such as the sounding of an alarm 98 or the de-energization of the generator either temporarily as described in the aforesaid patent application Ser. No. 520,269 or permanently until the discontinuity is attended to.

It is important to note that the foregoing detection circuitry is responsive to the sign of the currents flowing in the active and patient leads. That is, it detects only the active lead current substantially exceeding the patient lead current and not vice versa. Thus, the reference voltage of source 78 may be −5 volts, for example. Only when the voltage applied from resistor 80 is less then −5 volts will comparator 76 trigger SCR 90. Thus, if a patient circuit discontinuity occurs, the current flowing through diode bridge 70 will stop. However, the current flowing through diode bridge 62 will continue and the negative potential across resistor 72 will increase until this potential is sufficient to trigger the comparator. Normally, the current flowing through diode bridge 70 would offset the flow through diode bridge 62 and thus the potential across resistor 70 would remain at about ground level, which level would, of course, be insufficient to trigger the comparator.

There are surgical procedures where it is desirable to have two different generators with their respective electrosurgical instruments in contact with the patient where one of the generators is energized and the other idle. In this case, the current from the active generator would divide between its own patient electrode and the patient electrode for the idle generator. Thus, the current flowing in the patient lead of the idle generator would exceed that flowing in the active lead therefor. In safety circuits such as that disclosed in the aforementioned U.S. Pat. No. 3,683,923 or the application Ser. No. 520,269, this condition would trigger a nuisance alarm — that is, the signalling of an alarm when the patient is not in danger. However, in the present invention, this would mean that the current flowing in diode bridge 70 substantially exceeds that flowing in diode bridge 62. Hence, the potential across resistor 72 would positively increase with respect to ground. However, this simply drives the voltage across resistor 72 further away from the voltage needed to trigger comparator 76. Hence, as stated above, the detection circuitry of the present invention is effectively sensitive to the sign of the currents flowing in the active and patient leads whereby only a substantial excess of active lead current with respect to patient lead current is detected to trigger alarm 98 or to take some other appropriate measure.

A high level of performance is quite often desired of radio frequency generator 10. This might mean for coagulation waveforms, for example, that a high crest factor is employed together with a high peak-to-peak voltage where the amplitude level of the output signal may be adjusted. A generator for producing such waveforms is disclosed, for example, in U.S. Pat. No. 3,963,030, granted June 15, 1976 to David W. Newton, which is hereby incorporated herein by reference.

Leakage currents through stray capacitance 40 increase with high performance waveforms of the above type due to the high level of the waveform together with the higher harmonic content thereof where the amount of leakage current increases as the level of the output signal increases. The path followed by this current extends through stray capacitor 40 to ground and then through capacitor 46, resistor 44, capacitor 38, secondary winding 16 and then primary winding 54 back to the stray capacitance 40. Thus, the current flowing through winding 54 tends to exceed the current flowing through winding 58 by an amount corresponding to the leakage current. Further, as the level of the output signal from the generator 10 increases, the amount that the current through winding 54 exceeds that in winding 58 increases. The additional current flow caused by the leakage current through diode bridge 62 is of such a polarity as to move the voltage across resistor 62 toward the threshold or reference voltage for comparator 76. Hence, there is a danger of nuisance trips occurring because of the leakage current.

To offset and compensate for the leakage current, secondary winding 18 is provided on transformer 12 and couples current to a rectifier bridge 100 through a variable capacitor 102. The polarity of the current through the bridge 100 is opposite to that through bridge 62 and offsets the increase in the current through bridge 62 due to leakage current through stray capacitance 40. In particular, the variable capacitance 102 is adjustable over a range corresponding to the value of the leakage capacitance 40. The leakage capacitance may typically be about 80 pf while the variable capacitor 102 may extend over a range of about 2.4 through 24.5 pf. The value to which variable capacitor 102 is set so corresponds to the value of the stray capacitance 40 that the current flowing through diode bridge 100 substantially equals any increase in the current flowing through diode bridge 62 due to leakage current. It should be noted that, as the output level of generator 10 is changed, the leakage current will change and the corresponding offset current through bridge 100 will also change since the voltage coupled across secondary winding 18 corresponds to the voltage applied to the active lead to generate the leakage current. Thus, the circuitry including secondary winding 18, variable capacitor 102 and bridge 100 effectively provides a dynamically variable offset. Thus, the fixed threshold established by reference voltage 78 has the variable offset of bridge 100 added thereto so that the comparator 76 will not trigger until the difference between the active lead current and the patient lead current exceeds a dynamically variable threshold comprising the fixed threshold of source 78 plus the variable offset of bridge 100. Hence, variations in the setting of the output level of the radio frequency generator are compensated for in the safety circuit of the present invention, whereby the fixed threshold established by reference source 78 can be set as low as possible without danger of nuisance trips. By setting the fixed threshold as low as possible, patient safety is enhanced.

Referring to frequency sensitive network 42, the purpose thereof is to provide a high impedance path to ground from the patient lead for power frequencies and the like while maintaining a low impedance path for radio frequencies. The impedance path at power frequencies and the like should be high because of the possibility of the patient being contacted by a faulty piece of equipment at a large, low frequency potential. If patient lead 26 were at ground potential in this frequency range, extremely hazardous current could flow through the patient to ground through electrode 44 and lead 26. To avoid this, the value of capacitor 46 is chosen to be sufficiently low at power frequencies to thereby establish the desired high impedance path between the patient lead and ground. As will be brought out in more detail hereinafter, secondary winding 22 on transformer 12 may be utilized to further lower the value of the capacitor 46 to thereby achieve greater isolation of lead 26 from ground at power frequencies.

The value of capacitor 46 at radio frequencies is high enough that a low impedance is established between the patient lead and ground thereby effectively keeping the patient at a low potential. Heretofore, in the prior art, isolated output circuits have been employed where the patient lead was isolated from ground at both power and radio frequencies. The potential on the patient could thus rise to undesirably high levels for different reasons. For example, if the active electrode 30 inadvertently came in contact with a grounded object, the full output voltage of the generator would be applied across the patient. Further, high leakage currents through the active lead-to-ground stray capacitance and then back through the patient lead-to-ground capacitance could also raise the potential on the patient to such a level that a person such as an anesthesiologist lightly touching the patient could experience a slight, disconcerting burning sensation.

In the present invention, these problems are minimized by providing the low impedance, radio frequency path established by frequency sensitive network 42, the impedance of this path being substantially less than that of the stray capacitance 104 from the patient lead 26 to ground.

A frequency sensitive network of the foregoing type has previously been disclosed in the aforementioned patent application Ser. No. 520,269. In accordance with the present invention, the effectiveness thereof can be enhanced by the use of secondary winding 22 of transformer 12 and condensor 106 whereby current is directed through capacitor 46, the latter current being out of phase with that flowing through this capacitor due to the current flowing from active electrode 30. As stated before, the current from electrode 30 normally divides between two paths, one of which includes frequency sensitive network 42. The amount of current provided from secondary winding 22 and capacitor 106 should be some portion of the maximum amount of current expected to flow through capacitor 46 due to the current flowing from active electrode 30 — that is, the current which would be flowing when the comparator 76 is triggered to indicate an alarm condition. Typically the offset current would be about ½ of this maximum current and would thus reduce the potential on lead 26 to a value that could be tolerated on the patient even when close to the maximum current was flowing. The value of the capacitor 46 is typically 1500 pf. However, if the circuit including transformer 22 and condensor 106 were not employed, this value would have to be increased to about 2500 pf to ensure a sufficiently low potential on the patient when near maximum current was flowing. Typically, the potential on the patient should not exceed 30 volts. Thus, the value of capacitor 46 may be decreased to a smaller value to thereby enhance patient isolation from ground at power frequencies while at the same time keeping the radio frequency potential on the patient at a value less than 30 volts, for example.

Illustrative but non-limiting values which may be employed for the components of the circuit of the drawing, where all capacitor values are in microfarads and all resistor values are in ohms, ±10%, ½ watt, unless otherwise specified, are as follows:

Capacitors 36 and 38: 0.0047, 6KV
Resistor 44: 100, 3W
Capacitor 46: 1500 pf, 6KV
Resistor 72: 5.6K
Capacitor 74: 0.33, 50V
Reference voltage source 78: −5V
Resistor 80: 100K
Capacitor 82: 0.1, 50V
Resistor 84: 120K
Resistor 86: 10K
Capacitor 88: 0.01, 100V
SCR 90: MCR 104
Resistor 92: 2.2K
Capacitor 94: 0.1, 100V
Resistor 96: 10K
Capacitor 102: 2.4 – 24.5 pf

What is claimed is:
1. An electrosurgical generator comprising
a radio frequency generator;
an electrosurgical instrument having an active electrode suitable for application to a patient;
an active lead connected between said generator and said active electrode for conducting current from said generator to said active electrode;
a patient electrode adapted for connection to said patient to provide a low impedance path for current from said active electrode;
a patient lead connected between said generator and said patient electrode for conducting current from said patient electrode back to said generator; and
a safety circuit means for detecting only an excess of active lead current with respect to patient lead current to thereby indicate a discontinuity in a patient circuit including said patient electrode and said patient lead;
the level of the output signal from said radio frequency generator being adjustable and said safety circuit means detecting an excess of current in the active lead with respect to current in the return lead and including threshold means for indicating an alarm condition when the active lead current exceeds the patient lead current by a threshold level established by said threshold means, said threshold means including compensating means for dynamically varying said threshold level, said compensating means being responsive to adjustments in the output signal level of said generator to make said safety circuit means responsive to expected differences of said active and patient lead currents under normal conditions to thereby both provide a sensitive threshold in a variety of conditions and to offset the tendency of said signal adjustments to prematurely generate said alarm condition when there is no danger to said patient.

2. An electrosurgical generator as in claim 1 where said safety circuit means detects the difference between the active lead current and the patient lead current and where said compensating means generates an offset current which is a function of leakage current which flows through stray capacitance from the active lead to ground, said compensating means including means for subtracting said offset current from the said difference between the active lead current and the patient lead current detected by said safety circuit means.

3. An electrosurgical generator as in claim 2 where said safety circuit means includes
   active lead monitoring means for sensing the current in said active lead;
   patient lead monitoring means for sensing the current in the patient lead;
   active current rectifying means for rectifying the current sensed in the active lead by the active lead monitoring means;
   patient current rectifying means for rectifying the current sensed by said patient lead monitoring means;
   means for substracting from one another the rectified currents produced by said active and patient current rectifying means; and
   detecting means for indicating only when the rectified active lead current exceeds the rectified patient lead current.

4. An electrosurgical generator as in claim 3 where said compensating means includes compensating rectifying means and coupling means for coupling a portion of the output current from said radio frequency generator to said compensating rectifying means which is responsive thereto to generate said offset current, said offset current being subtracted from the difference between the rectified active lead current and the rectified patient lead current to thereby offset said tendency of said signal adjustments to prematurely generate said alarm condition.

5. An electrosurgical generator as in claim 4 where said coupling means includes a variable capacitor, the value of which may be set to a value corresponding to the value of said stray capacitance from the active lead to ground.

6. An electrosurgical generator as in claim 1 including a frequency sensitive alternate current return path connected between said patient lead and ground, the impedance of said path being high at low frequencies and low at the output frequencies of the radio frequency generator, the current through said last mentioned path being a function of the difference between the active lead current and the patient lead current where said safety circuit means indicates the level of the radio frequency current flowing through said alternate current return path.

7. An electrosurgical generator as in claim 6 where said frequency sensitive alternate current return path has a capacitor disposed therein and where said electrosurgical generator includes voltage decreasing means for decreasing the voltage across said capacitor so that said capacitor may have a small value of capacitance to thereby establish a higher, low frequency impedance to ground while at the same time maintaining the voltage on said patient lead at a level which is not hazardous to the patient.

8. An electrosurgical generator as in claim 7 where said voltage decreasing means includes means for coupling a portion of the output current from said radio frequency generator to said capacitor, said last mentioned current being out of phase with the current flowing through said capacitor due to the active lead current whereby the voltage across said capacitor is decreased.

9. An electrosurgical generator comprising
   a radio frequency generator, the level of the output signal of which is adjustable;
   an electrosurgical instrument having an active electrode suitable for application to a patient;
   an active lead connected between said generator and said active electrode for conducting current from said generator to said active electrode;
   a patient electrode adapted for connection to said patient to provide a low impedance path for current from said active electrode;
   a patient lead connected between said generator and said patient electrode for conducting current from said patient electrode back to said generator;
   a safety circuit means for detecting an excess of current in the active lead with respect to current in the return lead including threshold means for indicating an alarm condition when the active lead current exceeds the patient lead current by a threshold level established by said threshold means; and
   said threshold means including compensating means for dynamically varying said threshold level, said compensating means being responsive to adjustments in the output signal level of said generator to offset the tendency of said signal adjustments to prematurely generate said alarm condition when there is no danger to said patient.

10. An electrosurgical generator as in claim 9 where said safety circuit means detects the difference between the active lead current and the patient lead current and where said compensating means generates an offset current which is a function of leakage current which flows through stray capacitance from the active lead to ground, said compensating means including means for subtracting said offset current from the difference between the active lead current and the patient lead current detected by said safety circuit means.

11. An electrosurgical generator as in claim 10 where said safety circuit means includes
   active lead monitoring means for sensing the current in said active lead;
   patient lead monitoring means for sensing the current in the patient lead;
   active current rectifying means for rectifying the current sensed in the active lead by the active lead monitoring means;
   patient current rectifying means for rectifying the current sensed by said patient lead monitoring means;
   means for substracting from one another the rectified currents produced by said active and patient current rectifying means; and
   detecting means for indicating only when the rectified active lead current exceeds the rectified patient lead current.

12. An electrosurgical generator as in claim 11 where said compensating means includes compensating rectifying means and coupling means for coupling a portion of the output current from said radio frequency generator to said compensating rectifying means which is responsive thereto to generate said offset current, said offset current being subtracted from the difference between the rectified active lead current and the rectified patient lead current to thereby offset said tendency of said signal adjustments to prematurely generate said alarm condition.

13. An electrosurgical generator as in claim 12 where said coupling means includes a variable capacitor, the value of which may be set to a value corresponding to the value of said stray capacitance from the active lead to ground.

14. An electrosurgical method comprising the steps of generating a radio frequency signal from a radio frequency generator;

applying an electrosurgical instrument having an active electrode to a patient;

conducting current from said generator to said active electrode through an active lead;

connecting a patient electrode to said patient to provide a low impedance path for current from said active electrode;

conducting current from said patient electrode back to said generator through a patient lead;

detecting an excess of active lead current with respect to patient lead current to thereby indicate a discontinuity in a patient circuit including said patient electrode and said patient lead;

the level of the signal from said radio frequency generator being adjustable and where detecting step detects an excess of current in the active lead with respect to current in the return lead and indicates an alarm condition when the active lead current exceeds the patient lead current by a threshold level, said method including the step of dynamically varying said threshold level to offset the tendency of adjustments in the level of the generated radio frequency signal to cause unwanted alarm conditions or increases in said threshold level.

15. An electrosurgical method as in claim 14 including providing a frequency sensitive alternate current return path connected between said patient lead and ground having a capacitor disposed therein, the impedance of said path being high at low frequencies and low at the output frequencies of the radio frequency generator, the current through said last mentioned path being a function of the difference between the active lead current and the patient lead current where said detecting indicates the level of the radio frequency current flowing through said alternate current return path; and decreasing the voltage across said capacitor by applying current thereto out of phase with the current flowing therethrough due to the current in the active lead so that said capacitor may have a small value of capacitance to thereby establish a higher, low frequency impedance to ground while at the same time maintaining the voltage on said patient lead at a level which is not hazardous to the patient.

* * * * *